(12) United States Patent
Buchholz et al.

(10) Patent No.: US 10,130,827 B2
(45) Date of Patent: *Nov. 20, 2018

(54) ENHANCEMENT OF PENETRATION AND ACTION

(71) Applicant: Merck Patent GmbH, Darmstadt (DE)

(72) Inventors: Herwig Buchholz, Frankfurt am Main (DE); Ewald Aydt, Rossdorf (DE); Junyou Pan, Frankfurt am Main (DE)

(73) Assignee: Merck Patent GmBh (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/403,568

(22) Filed: Jan. 11, 2017

(65) Prior Publication Data

US 2017/0182333 A1  Jun. 29, 2017

Related U.S. Application Data

(63) Continuation of application No. 13/810,322, filed as application No. PCT/EP2011/003031 on Jun. 20, 2011, now Pat. No. 9,597,527.

(30) Foreign Application Priority Data

Jul. 17, 2010  (EP) .................................... 10007426

(51) Int. Cl.
*A61N 5/06*  (2006.01)

(52) U.S. Cl.
CPC .... *A61N 5/0616* (2013.01); *A61N 2005/0645* (2013.01); *A61N 2005/0652* (2013.01);
(Continued)

(58) Field of Classification Search
CPC ... A61M 2037/0007; A61N 2005/0645; A61N 2005/0652; A61N 2005/0653;
(Continued)

(56) References Cited

U.S. PATENT DOCUMENTS 5,957,960 A    9/1999  Chen et al.
7,135,033 B2 * 11/2006  Altshuler ............. A61B 18/203
                                                   607/88
(Continued)

FOREIGN PATENT DOCUMENTS

JP    3-111528 B2    11/2000
JP    3-191957 B2     7/2001
(Continued)

OTHER PUBLICATIONS

Japanese Office Action Translation for Application No. 2016-042325, dated Dec. 20, 2016.
(Continued)

*Primary Examiner* — Deanna K Hall
(74) *Attorney, Agent, or Firm* — Drinker Biddle & Reath LLP

(57) ABSTRACT

The present invention relates, inter alia, to dermal systems comprising at least one light source and at least one pharmaceutically and/or cosmetically active ingredient. The dermal systems can be employed in order to enhance the penetration and action of the pharmaceutically and/or cosmetically active ingredient.

17 Claims, 2 Drawing Sheets

(52) U.S. Cl.
CPC ............... *A61N 2005/0653* (2013.01); *A61N 2005/0656* (2013.01); *A61N 2005/0659* (2013.01); *A61N 2005/0663* (2013.01)

(58) Field of Classification Search
CPC .... A61N 2005/0656; A61N 2005/0659; A61N 2005/0662; A61N 5/0616; A61N 5/062
USPC .......................................................... 604/20
See application file for complete search history.

(56) References Cited

U.S. PATENT DOCUMENTS

| | | | |
|---|---|---|---|
| 7,304,201 B2* | 12/2007 | Holloway | ............... A61F 15/00 602/41 |
| 2009/0198173 A1 | 8/2009 | Samuel et al. | |
| 2009/0281048 A1 | 11/2009 | Pitcher | |
| 2010/0114007 A1 | 5/2010 | Fischer | |

FOREIGN PATENT DOCUMENTS

| | | |
|---|---|---|
| JP | 2001527446 A | 12/2001 |
| JP | 2003-284757 A | 10/2003 |
| JP | 2004-358063 A | 12/2004 |
| JP | 2007044091 A | 2/2007 |
| JP | 2009-536045 A | 10/2009 |
| WO | WO-2006/012752 A1 | 2/2006 |
| WO | WO-2010078581 A1 | 7/2010 |

OTHER PUBLICATIONS

International Preliminary Report on Patentability for PCT/EP2011/003031, dated Jan. 22, 2013.
International Search Report for PCT/EP2011/003031, dated Sep. 8, 2011.
EPO Form 2001, European Application No. 11726713.8-1652, dated Jan. 20, 2014.

* cited by examiner

ENHANCEMENT OF PENETRATION AND ACTION

The present invention relates inter alia to a dermal system comprising a light source in order to enhance penetration and/or action of pharmaceutically and/or cosmetically active ingredients through human and/or animal skin.

Active ingredients are administered to the human or animal body in many different ways. Three well established routes of administration are oral, injection (e.g. intravenous), and via the skin such as topical and transdermal. Oral administration of active ingredients is often considered to be the most convenient one for patients. However, often high doses of active ingredients have to be administered in order to achieve the desired effect. This is mainly due to the fact that oral bioavailability is often very low, for example because of loss of active ingredient because of low absorption in the gastrointestinal (GI) tract and the first pass effect. Thus, the doses applied have to be high in order to achieve the desired effect at the side of action. These, at least principally, unnecessarily high concentration of an active ingredient or the occurrence of its metabolites can cause unwanted side effects, even if they are not absorbed in the GI tract. An increased bioavailability of the active ingredient can reduce its unwanted side effects. Beside some few exceptions (e.g. treatment of diabetes), administration by injection is still mainly focussed on therapies carried out by medical professionals in hospitals or doctor's practice. Furthermore, administration by injection is still not well accepted by patients. Many patients feel uncomfortable to receive an active ingredient by injection. Transdermal patches or plasters can also be employed for systemic therapy strategies. The skin is very effective as selective penetration barrier. Percutaneous absorption involves the passage of the active ingredient from the skin surface into the stratum corneum (SC) under the influence of a concentration gradient and its subsequent diffusion through the SC and underlying epidermis, through the dermis, and into the blood circulation. The skin behaves as a passive barrier to the penetrant molecule and the SC provides the greatest resistance to penetration, and is the rate limiting step in percutaneous absorption. In the therapy of various diseases, transdermal therapeutic systems (TTS) have been introduced on the market. Examples are fentanyl plaster for the treatment of pain, nitroglycerol plaster for the treatment of angina, plaster comprising estrogen and testosterone for hormone replacement therapy, and plaster comprising nicotine for the use in nicotine replacement therapy. The transdermal route of application is, however, limited to a relatively small number of active ingredients which are capable to penetrate the SC. The same is valid for dermal applications of topical active ingredients. The delivery of active ingredients with low penetration rates through the SC can, at least in part, be enhanced by the use of penetration enhancers.

Penetration enhancers are substances that facilitate the absorption of penetrant through the skin by temporarily diminishing the impermeability of the skin. Ideally, these materials should be pharmacologically inert, non toxic, and non-irritating non-allergic. Although at least some of the penetration enhancers used fulfil these requirements the penetration enhancers only work with a relative small number of active ingredients and can therefore not be used in general.

One of the main advantages with transdermal systems is, that slow release can be achieved without an unnecessary high systemic concentration peak followed by a rapid decrease of the systemic concentration. Transdermal systems, thus, allow the systemic level of an active ingredient to be on a relative constant level. Furthermore, the dose of active ingredient required to achieve the constant level is, in many cases, much lower as compared to the dose required in an oral route of administration.

W.-R. Lee et al. have shown (Lasers Med. Sci. 2007, 22:271-278) that the penetration of three narcotic analgesics can be enhanced by a factor of 10 to 35 if the skin is pre-treated with an irradiation having a wavelength of 2940 nm. The authors performed an in vitro pig skin penetration experiment to evaluate the action of pulsed laser light emitted by an erbium:-yttrium-aluminium-garnet (ER:YAG) laser. The skin was pre-treated with the laser followed by the treatment with either morphine, nalbuphine, and buprenorphine. The authors show that transdermal delivery was greatly enhanced by removing a portion of the SC by the laser. Thus, this method is not suitable for portable, user friendly applications and are likely to require the intervention and monitoring of medical professionals.

N. Otberg et al. have shown in GMS German Medical Science 2008, 6, 1-14 showed that water-filtered infrared-A (wIRA) can act as penetration enhancer for topically applied substances. Based on investigation with 12 test persons, the authors suggest the application of wIRA as penetration enhancer for even hydrophilic substances. They also suggest the method to be applied to wider range of substances. However, that authors do not provide technical solutions for a user friendly, portable device. The authors use a large device (Hydrosun®) which is only suitable for non-portable application.

Current transdermal systems and dermal patches (commonly referred herein as to dermal systems) which are intended to deliver an active ingredient into the skin, rather than delivering it to the systemic circulation, however, suffer from a couple of problems. As already mentioned above they are limited to a relatively small number of active ingredients that are capable to cross the skin barrier. In addition, the doses of active ingredients applied in current therapies based on dermal systems are often rather high, in order to compensate the loss of active ingredients in the course of transport of the active ingredient through or into the skin. The required concentration at the site of action of an active ingredient can, thus, in many cases only be obtained if the applied dose is high enough. The relatively high dose, in turn, may results in unwanted side effects on the skin (e.g. irritation of the skin), in the skin, and/or in other tissues. In addition, active ingredients which are currently administered topically by the use ointment, oils, gels, cremes, emulsions, miniemulsions, lotions, and other formulations of i.e., without employing a dermal patch or transdermal plaster/system, show high losses when applied to the area of the subject to be treated. The reason for the loss is manifold. First of all, low penetration may cause high losses of active ingredients. Furthermore, topically administered active ingredients may rapidly be wiped off by clothes, for instance.

One objective of the present invention is to provide a new dermal system which allows much wider application of topical/dermal and transdermal routes of administration for more pharmaceutically and/or cosmetically active ingredients (commonly referred herein as to active ingredients) as known in the prior art. Another objective of the present invention is to provide a user friendly system which is easy to handle and can be used without the control by a medical professional. Yet another objective of the present invention is to provide a way to reduce unwanted side effects of existing therapies.

Surprisingly it has been found that a dermal system can be used in order to enhance the penetration of a wide range of pharmaceutically and/or cosmetically active substances or ingredients wherein the dermal system comprises a light source comprising a thin light source selected from inorganic light emitting diodes (LEDs), organic light emitting diodes (OLEDs), polymer light emitting diodes (PLEDs), and organic light emitting electrochemical cells (OLECs or LECs). Herein the term "dermal system" relates to both the transport of active ingredients through the skin into, e.g., the blood circulation and the enrichment of topically applied active ingredients in the skin. The term "dermal system", thus, includes what is known as transdermal system and dermal patch (skin patch). The term dermal system also includes any current known treatment strategies where the active ingredient(s) are administered topically without employing a dermal patch or a transdermal plaster/system. The effect of achieving an enrichment of topically applied active ingredients can also be employed to get the desired therapeutic or cosmetic concentration of an active ingredient while lowering the dose of active ingredient on the skin. Therefore, the dermal system according to the present invention either allows to increase the concentration at the side of action or to the reduce the doses applied in order to keep the concentration at the side of action on the desired level, or to open the dermal route of administration to a much wider range of new active ingredients which haven't used for dermal applications before.

The term "dermal application" as used herein comprises the transdermal rout of administration and topical or dermal application.

The thin light sources employed allow the production of very thin devices used either stationary and preferably ambulatory. The device, such as a plaster, comprising the thin light source can be positioned directly under the clothes on the skin to be treated. The devices show further a homogenous illumination of the area to be treated. Intensities of the irradiation can be precisely adjusted and on a low level as compared to stationary devices. The device further may be flexible and thus allow optimal irradiation of curved areas, such as large wrinkles and/or curls. Furthermore, intensities, duration of irradiation, and emission wavelengths can be adjusted easily with a minimum of human interaction and without the need to consult a specialist, such as a physician.

The present invention relates to a dermal system comprising at least one light source and at least one pharmaceutically and/or cosmetically active ingredient used for the enhancement of penetration and/or action of at least one of the pharmaceutically and/or cosmetically active ingredients.

The present invention also relates to a dermal system comprising at least one light source and at least one pharmaceutically and/or cosmetically active ingredient used for the enhancement of penetration of at least one of the pharmaceutically and/or cosmetically active ingredients.

Preferably the light source is a thin light source. Particularly preferably the thin light source comprises at least one light emitting diode (LED). The light emitting diode may be an inorganic LED or an organic LED. In a preferred embodiment the said at least one LED is an organic LED (OLED) and/or polymer light emitting diode (PLED).

Preferably the dermal system comprises 3, particularly preferably 2, and very particularly preferably 1 thin light source(s).

Preferably the light source comprises 3, particularly preferably 2, and very particularly preferably 1 light emitting diodes or organic light emitting device(s).

In a particularly preferred embodiment of the present invention the dermal system comprises exactly one thin light source comprising one organic light emitting device, preferably an OLED.

In a particularly preferred embodiment of the present invention the dermal system comprises exactly one thin light source comprising one organic light emitting device, preferably an OLEO.

The terms active ingredient(s) and pharmaceutically and/or cosmetically active ingredient are, if not stated otherwise, used synonymously herein.

The dermal system is capable to enhance both the penetration of the pharmaceutically and/or cosmetically ingredient and the action of them. The radiation emitted by the dermal system leads to an enhanced penetration of pharmaceutically and/or cosmetically ingredients without disturbing the integrity of the skin, which is of importance to fulfil protection functions. Further mechanisms on how the dermal system enhances penetration are possible and the present invention is not limited to any mechanism. Through the enhancement of penetration the drug action is also enhanced. This is, e.g., due to the higher penetration rate leading to a higher concentration in the tissue and/or to a deeper penetration into the tissue. The enhancement of drug action may also be based on a synergistic effect between the well known beneficial effect of red light or infrared irradiation on the skin and the beneficial pharmaceutical and/or cosmetic action of the active ingredients. The dermal system can, thus, lead to both an increased concentration of the pharmaceutically and/or cosmetically ingredient(s) at the side of action in a specific area of the skin and/or a deeper penetration of pharmaceutically and/or cosmetically ingredients trough the skin into, e.g., the systemic circulalion or other tissues.

The dermal system can also be used, as outlined above, to reduce side effects of the pharmaceutically and/or cosmetically ingredients by reducing the doses required to get the required concentration at the side of action. In other cases the dermal system can be used in order to increase the systemic level of pharmaceutically and/or cosmetically ingredients and/or to decrease the administered doses required in order to get the required systemic concentrations.

The dermal system according to the present invention can, thus, be used to increase the penetration rate of systemically and/or topically acting ingredients.

The dermal system can principally be applied to any pharmaceutically and/or cosmetically active ingredient, no matter if it is currently used for transdermal or topical application or not. The said dermal system can therefore be used in order to make the transdermal or topical route of administration accessible for both hydrophobic and hydrophilic active ingredients that have not been considered for transdermal or topical application before.

Preferably the said dermal system comprises at least one pharmaceutically and/or cosmetically active ingredient that is already known to be administered by transdermal or topical application.

Indeed the said dermal system can be used for a wide range of active ingredients. The active ingredients can be selected from pharmaceutically active ingredients and/or cosmetically active ingredients including oils from natural sources.

Preferably the dermal system according to the present invention comprises at least one active ingredient selected from fluidextract of comfrey radix, particularly fluidextract of symphytum officinale radix (Kytta-ointment®, Kytta-balsam®, Kytta-plasma®, and Kytta-lotion®).

Further preferred active ingredients for the dermal system according to the present invention include those which are usually administered topically, for example, are diclofenac, ketorolac, ketoprofen, ibuprofen, ketofifen, methylphenidate, aceclofenac, capsaicin, heparin, oxybutynine, epinephrine, campher, vipers ammodytes toxin, extract from arnica montana, indomethacin, vitamins, preferably vitamine D and vitamine $B_{12}$, estrogen, testosterone, progesterone, estradiol, ethinylestradiol, chondoitinpolysulfate, etofenamat, flufenamic, caffeine, nicotine, nitroglycerol, scopolamine, rotigotine, rasagiline, alprazolam, bisoprolol, estrogen, rivastigmine, clonidine, buprenorphine, fludroxycortide, viscum album, mandragora, apisinum, bufexamac, acemetacin, azapropazone, celecoxib, dexketoprofen, diflunisal, etodolac, etoricoxib, fenbufen, fenoprofen, flurbiprofen, indometacin, ketoprofen, mefenamic acid, meloxicam, nabumetone, naproxen, piroxicam, rofecoxib, sulindac, tenoxicam, tiaprofenic acid, valdecoxib, glyceryl trinitrate, opioids such as fentanyl buprenorphine, salicylic acid and related salicylates; or any agent used as a local anaesthetic, for example lignocaine, lidocaine and prilocaine, bupivacaine, levobupivacaine, procaine, ropivacaine, tetracaine, benzocaine or amethocaine, fusidic acid, betamethasone and derivatives and/or combinations therof Examples of natural oils that can be used as active ingredient in the dermal system according to the present invention are, without limitation, peppermint oil, eucalyptus oil, oil from rosemary, and lavender oil.

Based on the disclosure of the present invention many further active ingredients can be added to the lists herein without being inventive.

As already outlined the dermal and, thus, also the transdermal system may comprise more than one active ingredient, provided that they are compatible with one another under conditions of storage and use.

Components which are commonly used as a base for creams, ointments or gels may be used as a carrier medium in the active ingredients according to the present invention. These components include: water; hydrocarbon oils and waxes; silicone oils; vegetable, animal or marine fats or oils; glycerides (such as, for example, or more glycerol esters of saturated fatty acids or polyglycolysed glycerides, cocoa butter, theobroma or the like) or glyceride derivatives; high molecular weight polyethylene glycol, polyoxyethylene, lanolin and derivatives thereof; fatty acids, fatty alcohols or fatty esters (including, for example, caprylic acid, caprylic triglyceride or the like); lecithin; polyhydric alcohols or esters; wax esters; sterols; phospholipids and the like. Thickening agents such as gums or other forms of hydrophilic colloids may be included. The carrier medium may comprise more than one base component.

Where the active ingredient(s) are formulated as a cream, the carrier medium may comprise substantially more oil based components than water. Where the active ingredient(s) are formulated as an ointment, the carrier medium may comprise substantially more water than oil based components. Where the active ingredients are formulated as a gel, the carrier medium may substantially comprise water.

Furthermore the dermal systems according to the present invention may comprise one or more film forming materials Methods for softening as may be required for dermal system according to the present invention are disclosed in WO 02/00203.

The dermal system according to the present invention may further comprise, where appropriate, additional ingredients such as one or more penetration enhancers (which may be surfactants, alcohols, esters, glycols or the like or any other suitable penetration enhancer), humectants, surfactants (which may be cationic, non-ionic, anionic or polymeric), emulsifiers, antioxidants, preservatives, clays, antifoaming agents, spreading agents, emollients, barriers, solubilising agents for the active ingredient and the like.

The dermal system according to the present invention may also comprise solvents, such as ethanol, menthol, thymol, eucalyptol, eucalyptus oil, benzyl alcohol, isopropyl alcohol, propylene glycol, methylated spirit, phenol, cyclodextrins, ethyl oleate, eugenol, glycerol, levomenol, monoethanolamine oleate, myristyl alcohol, octyldodecanol, methyl alcohol, coconut oil or silicone oil.

The presence of solvents in the dermal system according to the present invention allows controlled transdermal administration of the therapeutic agent. The extent to which, and speed with which local and systemic administration of a therapeutic agent from a topically applied composition occurs is associated with the depth and rate of penetration of the active ingredient through the skin.

The dermal system according to the present invention may further comprise organoleptic agents to improve the organoleptic properties of the composition. Such agents include almond oil, glycerol, linseed oil, monoethanolamine oleate, grape oil, mace oil, isopropyl myristate, isopropyl palmitate, palm kernel oil, theobroma oil, wool alcohols. The inclusion of organoleptic agents can be used, for example, to enhance the feel of the dermal system, which can improve patient compliance. In addition, such agents can have a perceived cooling effect, which can provide a positive psychological effect, particularly, for example, in the case of application to an inflamed joint.

The dermal system according to the present invention may further comprise sensory cues, such as anise oil, citronella oil, clove oil, eucalyptol, eucalyptus oil, eugenol, juniper oil, lemon grass oil, lemon oil, terpeneless lemon oil, melaleuca oil, neroli oil, nutmeg oil, olive oil, orange oil, terpeneless orange oil, poppy seed oil, pine oil, rose oil, sage oil, spearmint oil, lavender oil, thyme oil, vanillin.

The inclusion of such cues in the dermal system can provide the patient with pleasant sensory feedback upon use, allows the patient and/or person applying the dermal system to recognize that administration has occurred, and may aid recollection of administration. Such factors can improve patient compliance and provide a positive psychological effect.

The dermal system according to the present invention may further comprise insect repellents such as citronella or lemon grass.

The use of preservatives can be undesirable, as they may provoke allergic reactions in susceptible patients, and the present invention may be advantageous in avoiding or reducing the risk of such allergic reactions. Preservatives that have been associated with allergic reactions include chlorocresol, hydroxybenzoates (parabens), polysorbates, sorbic acid and the like, and these preservatives are included in a large number of known topical compositions.

Further details on materials commonly used in dermal systems are disclosed, e.g., in WO 2007/066148. Matrix materials used in particular in matrix systems are disclosed, e.g., in WO 87/00042 and WO 00/02539

Furthermore synergistic effects between the beneficial action of red light and/or infrared radiation and the pharmaceutically and/or cosmetically active ingredient can be observed, i.e. the well known beneficial irradiation with red and/or infrared light and the beneficial action of a pharmaceutically and/or cosmetically active ingredient can lead to a non-linear synergistic effect when applied concurrently.

Hereby, concurrent treatment includes totally and partly parallel and sequential treatment with light/radiation and active ingredient, i.e. the object to be treated can also be pre-treated with either light/radiation followed by the treatment with the active ingredient or vice versa.

Preferably the dermal system comprises 3, particularly preferably 2, and very particularly preferably 1 pharmaceutically and/or cosmetically ingredient(s).

Often the borders between therapeutic and cosmetic applications are vague and depend on individual circumstances and the assessment of a physician. Often therapeutic conditions are associated with cosmetic consideration. The treatment or prophylaxis of acne, for example, may have both therapeutic and cosmetic components, depending on the degree of the condition. The same accounts for psoriasis, atopic dermatitis and other diseases and/or conditions. Many diseases and conditions are associated with apparent implications which are often represented by a change in the visibility of a subject's skin, for instance. These cosmetic or aesthetic changes can often lead to psychological modifications resulting, at least in part, in serious diseases.

Some conditions or diseases may have an emphasis on cosmetic components, even if therapeutic elements may also play a role. Some of these are selected from anti-ageing, anti-wrinkle, the prevention and/or therapy of acne and vitiligo.

The present invention also relates to the uses of thin light sources as penetration enhancer for the pharmaceutically and/or cosmetically active ingredients as outlined elsewhere within the present application. The light sources that can be preferably used for this purpose are LEDs, OLEDs, PLEDs, and OLECs, particularly preferably OLEDs, PLEDs, and OLECs.

Preferably the penetration occurs via the skin wherein particularly preferably the skin of animals and humans is meant.

The dermal system according to the present invention can thus be The term dermal system according to the present invention does not include the concept of photodynamic therapy (PDT). In PDT an active ingredient is applied to the subject to be treated which is activated by irradiation of mostly short wavelengths. The active ingredient is photochemically activated and undergoes a chemical reaction. In many cases the precursor is pharmaceutically and/or cosmetically inactive whereas the irradiation initiates the conversion from an more or less inactive state into an active state. PDT is mainly employed in order to treat cancer.

Preferably the said dermal system emits red light and/or irradiation in the infrared region. Thus, a dermal system according to the present invention characterized in that the light source emits red light with a maximum emission in the range between 580 and 700 nm and/or infrared irradiation with a maximum emission in the range between 700 nm and 3 mm is also subject of the present invention. Particularly preferably the irradiation emitted has its maximum wavelength in the range between 700 and 4000 nm and very particularly preferably in the range between 700 and 1400 nm. In a particularly preferred embodiment of the present invention the dermal system emits irradiation with wavelengths in the range between 780 nm and 1400 nm (infrared A).

In yet another preferred embodiment the dermal system also emits, in addition to the infrared irradiation visible light in the range between 590 nm and 700 nm.

Particularly preferably the dermal system according to the present invention emits light and irradiation in the range between 590 nm and 1400 nm.

In a preferred embodiment, the light source can be an IR-OLED. Any emitter, both fluorescent and phosphorescent emitter, which is know to the one skilled in the art, can be chosen as emitter in the emissive layer of the light source of the present invention. Examples are given to phospohrescent emitters comprising trivalent lanthanide cations ($Ln^{3+}$) that are chelated with chromophoric ligands to sensitize excitation energy transfer to the emissive lanthanide ion, as reported by O'Riordan et al. in Thin Solid Films (06), 497, p 299 and Schanze et al. in Synth. Met. (03), 137, p 1013, cyclometallated (pyrenyl-quinolyl)2Ir(acac) having $\lambda_{max}$=720 nm by William et al., in Appl. Phys. Lett. (06), 89, 083506/1, Pt porphyrin complex as reported by Borek et al. in Angew. Chem., Int. Ed. (07), 46, 1109, by Rozhkov et al., in Inorg. Chem. (03), 42, 4253, by Finikova et al., in J. Org. Chem. (05), 70, 4617. and by Brooks et al., in Dig. Tech. Pap.-Socinf. Dispint. Symp. (08), 39, 1975, and Thione Far-Red/Near-IR Triplet Emitters as reported by Evans et al., In J. Fluoresc. (09), 19, 169.

Any thin light source can be used in the dermal system according to the present invention. Preferable a thin light source has a thickness of less than 5 mm, particularly preferably less than 2 mm, and very particularly preferably less than 1 mm. Herein the term light source is used to define the light emitting device without any surrounding electronics, such as battery, adhesive elements, and switch. In case the dermal system comprises an OLED, for instance, the thickness of the light source is defined by the layer structure of the OLED, including, e.g., the hole and electron transporting/injecting layer, emissive layer, electrodes and encapsulation. In a preferred embodiment the present invention relates to said dermal system, characterized in that the organic light emitting device is selected from organic light emitting diodes (OLEDs), polymer light emitting diodes (PLEDs) and organic light emitting electrochemical cells (OLECs, also called LECs or LEECs).

OLEDs and PLEDs show the typical layer structure wherein, in general the number of layers in a device comprising small molecule organic functional materials is lower as compared to polymer light emitting devices. The organic functional materials used in OLEDs and PLEDs can be selected from any material typically employed by a skilled person in the field. OLEDs and PLEDs comprise, e.g., organic semiconductors, organic metal complexes, hole transport materials, hole injection materials, hole blocking materials, electron transporting materials, electron injection materials, electron blocking materials, exciton blocking materials, host materials, fluorescent and phosphorescent emitters, and dyes. Further the PLED and/or OLED comprises electrodes (cathode/anode) and is encapsulated. Typical structures of OLEDs and PLEDs as well as materials commonly used therein are disclosed, e.g., in WO 2004/058911 for OLEDs and WO 2008/011953 for PLEDs.

OLECs and materials used therein are also well known to one skilled in the art. In addition to materials used in OLEDs and/or PLEDs ionic materials are required for OLECs. In contrast to OLEDs and/or PLEDs, charge transport occurs via mobile ions in OLECs. Therefore materials such as ionic transition metals complexes (iTMCs) and/or ionic liquids are used in OLECs. More details on OLECs can be found, e.g., in Pei et al., Science, 1995, 269, 1086.

Typically the light sources selected from OLEDs, PLEDs, and/or OLECs have a planar or more or less planar layer structure. However, the structure of these light sources may also have the form of a fiber. Organic light emitting fibers have been published, e.g., in U.S. Pat. No. 6,538,375 B1, US 2003/0099858, and by Brenndan O'Connor et al. (Adv. Mater. 2007, 19, 3897-3900).

Said fibers facilitate the preparation of flexible and preferably plastic or ductile devices for the treatment of a subject. The wavelengths can be tailored easily and a homogenous irradiation of a subject is possible. In addition, by employing light emitting OLED, PLED and/or OLEC fibers the intensity and wavelengths) of light required for a specific treatment can be tailored by multiple factors. Intensity can, e.g., adjusted by the number of fibers used (i.e. the density of fibers), the way these fibers are processed or woven, and the voltage applied. The wavelength can also be adjusted easily. One fiber can comprise multiple emitter with peaks of emission at different wavelengths. The fiber can also comprise different segments comprising emitter materials with different emission peaks.

The term fiber as used herein means a shape having a length which is much greater than the cross sectional diameter (or width or height for non-circular cross sections). In a preferred embodiment of the present invention, the term fiber means a shape that has rather large length to diameter ratio, such as 10:1 or greater. Particularly preferably, the length to diameter ratio is 100:1 or greater.

The OLEDs used herein are electronic devices typically comprising the following sequence of layers:
optionally a first substrate,
an anode layer,
optionally a hole injection layer (HIL),
optionally a hole transport layer (HTL) and/or electron blocking layer (EBL),
an emissive layer (EML)
optionally an electron transport layer (ETL) and/or hole blocking layer (HBL),
optionally an electron injection layer (EIL)
a cathode layer,
optionally a second substrate.

Further, an OLED may comprise an exciton blocking layer between emissive layer and the electrode(s).

PLED is an OLED comprising emissive polymer in the emissive layer, which is usually deposited from solution. The typical PLED structure is anode/HIL or buffer layer/interlayer/EML/cathode. The interlayer has both hole transport and electron blocking properties. More details on PLED with interlayers are disclosed in WO 2004/084260 A2

Organic light emitting electrochemical cells (OLECs) comprise two electrodes, and a mixture or blends of an electrolyte and photoluminescent species in between, as firstly reported by Pei et al., Science 1995, 269, 1086. OLECs are similar to OLED with respect to layer structure, but remove the limit of selection of anode and cathode, and can comprise much thicker layer as compared to OLEDs.

The said light source may comprise any further materials which one skilled in the art would typically consider for the assembly of such a light source. These further materials include, e.g., color converting materials and/or color filter. Thus the present invention also relates to said dermal system, characterized in that the light source further comprises a down-conversion medium, which absorbs the light from the said light emitting device, and re-emits red light with a wavelength in the range between 580 and 700 nm and/or infrared radiation with a wavelength in the range between 700 nm and 3 mm.

If a color converter is employed in the dermal system according to the present invention any fluorescent and/or phosphorescent light emitting material can be used in order to get red light and/or infrared irradiation emitted by said dermal system.

In a preferred embodiment the color converter is used together with a fluorescent and/or phosphorescent light emitting material that emits light with an emission peak below 600 nm, particularly preferably below 560 nm, and very particularly preferably below 500 nm.

In another preferred embodiment the color converter is used together with a fluorescent and/or phosphorescent light emitting material and overall light in the range between 590 nm and 700 nm is emitted.

In another preferred embodiment the color converter is used together with a fluorescent and/or phosphorescent light emitting material and overall light and/or irradiation in the range between 700 nm and 1400 nm is emitted.

In another particularly preferred embodiment the color converter is used together with a fluorescent and/or phosphorescent light emitting material and overall light and/or irradiation in the range between 590 nm and 1400 nm is emitted.

The light source may also comprise inorganic materials which can be used for color converting.

Color Converter can be selected from phosphor materials, which may be used for example, for cathode-ray tubes and fluorescent display or lamps. Generally, the phosphor materials can be selected from yttrium oxide, yttrium tantalite, barium fluoride, cesium fluoride, bismuth germanate, zinc gallate, calcium magnesium pyrosilicate, calcium molybdate, calcium chlorovanadate, barium titanium pyrophosphate, a metal tungstate, a cerium-doped phosphor, a bismuth doped phosphor, a lead-doped phosphor, a thallium-doped sodium iodide, a doped cesium iodide, a rare earth-doped pyrosilicate, and a lanthanide halide.

In a preferred embodiment, the colour convert is a phosphor which has a narrow emission spectrum, especially for displayer applications. Such kind of phosphor can be selected from compounds comprising rare-earth recombination centres showing characteristic luminescence lines instead of bands due to the irradiation transition in the $4f^n$ shell which is well shielded electrically by 5d and 6s electrons. Preferably, such kind of phosphors have an absorption at wavelength 380 nm or more, and can be selected from, e.g., $Y_2O_3$:Sm, $Y_2O_3$:Eu, $Y_2O_3$:Dy and $Y_2O_3$:Ho, as disclosed by Lyuji Ozawa and Minoru Itoh in Chem. Rev. 2003, 103, 3836, and in the references therein. Further preferred phosphors can be selected from, but without limitation, ZnS:Cu,Al, ZnS:Cu,Au,Al, $Y_2O_2S$:Eu, $Y_2O_2S$:Eu, $Zn_2SiO_4$:Mn, $(KF,MgF_2)$:Mn, $(KF,MgF_2)$:Mn, $MgF_2$:Mn, $(Zn,Mg)F_2$:Mn, $Zn_2SiO_4$:Mn,As, $Gd_2O_2S$:Tb, $Y_2O_2S$:Tb, $Y_3Al_5O_{12}$:Tb, $Y_3(Al,Ga)_5O_{12}$:Tb, $Y_2O_3$:Eu, $InBO_3$:Tb, $InBO_3$:Eu, $Y_2SiO_5$:Tb.

In another preferred embodiment, the colour convert is a phosphor having a broad emission spectrum selected from, e.g., but without limitation, YAG:Ce, ZnS:Ag+(Zn,Cd)S:Cu, (Zn,Cd)S:Ag, (Zn,Cd)S:Cu, (Zn,Cd)S:(Cu,Cl), ZnS:Ag+(Zn,Cd)S:Cu, $Y_2O_2S$:Tb, (Zn,Cd)S:Cu,Cl+(Zn,Cd)S:Ag,Cl, ZnS:Ag+ZnS:Cu(or ZnS:Cu,Au)+$Y_2)_2S$:Eu, $InBO_3$:Tb+$InBO_3$:Eu+ZnS:Ag, $InBO_3$:Tb+$InBO_3$:Eu.

In a further embodiment, the present invention relates also to up-converting phosphors. Published phosphors of this kind are, e.g., nanophosphors comprising $NaYF_4$:Yb, Ln, wherein Ln is selected from the group consisting of Er, Ho and Tm as disclosed in WO 2009/046392

In a preferred embodiment of the present invention the said dermal system comprises the at least one pharmaceutically and/or cosmetically active ingredient and the said at least one thin light source in the same device. The device may be a plaster, a dermal plaster/patch or transdermal plaster, for instance, but any other device well known to one skilled in the art can be used. In a particularly preferred embodiment the dermal system as depicted in FIG. 1A is a device comprising a backing layer 1, a layer 2 comprising the light source 5 and a power supply 3, which may be a printed battery, and probably a steering unit 4. Furthermore the device comprises a self adhesive layer 6. Layer 6 is the reservoir comprising the active ingredient(s) dispersed preferably in a polymer matrix comprising one or more hydrophilic and/or hydrophobic polymers. The device also comprises a protecting foil 7 which can be removed when its use is intended. The light source 5 is, as outlined above preferably an OLED, PLED or OLEC. Preferably the matrix layer 6 is transparent.

In a further preferred embodiment of the present invention the said dermal system as depicted in FIG. 1B is a device comprising a backing layer 1, a layer 2 comprising the light source 5 and a power supply 3, which may be a printed battery, and probably a steering unit 4. Furthermore the device comprises a polymer layer 8 which is a reservoir comprising the active ingredient(s), a rate controlling microporous membrane 9, an adhesive layer 10 and a protecting foil 7.

The printed battery can be selected from, e.g., the "Soft Battery" by Enfucell Oy Ltd., Finland.

The dermal system comprising the at least one active ingredient may further comprise additional penetration enhancer. In principle any technique for enhancement of penetration known to a skilled person can be employed. The present invention also relates ton said dermal system comprising further chemical penetration enhancer such as ethanol, dimethyl sufoxide, derivatives of n-alkyl-azacycloheptanon (e.g. laurocapram, azone), fatty acids and esters of fatty acids (e.g. oleic acid, glycerolmonooleat, lauryllactat), 1,2-propylene glycol. The further penetration enhancer may be mixed with the active ingredient(s) in one layer or may be in a separate layer, preferably in the same layer.

In another preferred embodiment the dermal system according to the present invention comprises an additional layer between the layer 2 and the protecting foil 7. This additional layer acts as an absorbing layer which absorbs irradiation either in a broad range of wavelengths or specific wavelengths or both. One of the well known drawbacks of infrared irradiation is that it can cause dry skin. Irradiation in the infrared B and C region (IRB and IRC) may thus be filtered out from the light source. Furthermore, some specific wavelengths in the infrared A (IRA) region may also be unwanted in medical and/or cosmetic application. More specifically, irradiation having a wavelength or being close to 944 nm, 1180 nm, and/or 1380 nm may be filtered out. Different filters that can be used for this purpose are available and well known to one skilled in the art. One preferred filter that can be used according to the present invention is water. Water absorbs IRB and IRC irradiation and irradiation with 944 nm, 1180 nm, and 1380 nm. Preferably the layer comprising the water has a thickness of less than 5 nm, particularly preferably less than 3 mm, and very particularly preferably less than 2 mm. The filter layer may consist of pure water surrounded by, e.g., polyethylene. Furthermore the filter layer may comprise a hydrophilic formulation comprising water, such as a hydrogel (e.g. polyacrylicacid, derivatives of cellulose such as methylcellulose or carboxymethylcellulose, bentonite, aerosil), hydrophilic ointments (macrogoles comprising PEG, i.e. polyethyleneglycole), water comprising hydrophilic cremes (comprising e.g. Na-dodecylsulfate, polysorbate 20, 60, 80, macrogolstearate, cetylstearylalcohol). Water filtered IR irradiation can significantly enhance the penetration of even hydrophilic substances. One possible mechanism is the hydration of the stratum corneum, as shown by N. Otberg et al. have shown in GMS German Medical Science 2008, 6, 1-14. The dermal system according to the present invention can also be used in order to enhance the penetration of thermolabile active ingredients. This can be accomplished, e.g., by first pretreating the object to be treated with a device as depicted in FIG. 1C followed by the administration of the active ingredients on the same area of the subject to be treated without irradiating it further.

In yet another preferred embodiment the dermal system according to the present invention comprises a phosphor material which specifically emits the desired wavelength(s) in the infrared range, particularly in the IR-A range. Thus, the said dermal system comprises an emitter which emits light in the visible part of the spectrum which is absorbed by the phosphor material and re-emitted by the phosphor material in the IR-A range. Such kind of down-conversion can be accomplished with phosphors materials like $Al_xGa_{1-x}As$ or rare earth gallium aluminate (see FIG. 4).

The dermal system according to the present invention can also be composed of two different units. The first unit comprises the thin light emitting source which is preferably selected from LEDs, PLEDs, OLEDs, and OLECs, and particularly preferably PLEDs, OLEDs, and OLECs.

Preference is given to OLECs as light source. Further preference is given to OLEDs and PLEDs as light source. The second unit may be any formulation of the active ingredient(s), such as ointment, creme, gel, lipogel, hydrogel, liposome, emulsion, miniemulsion, powder, oil, paste, milk, or lotion. The second unit may be administered conventionally to the object to be treated, in particular to the skin of a human or animal. Afterwards the first unit may be attached to the object that: has been treated with the first unit. Preferably the second unit is placed at the same area that has been treated before with the first unit. Thus the present invention also relates to the use of thin light sources, preferably LEDs, OLEDs, PLEDs, and OLECs, particularly preferably OLEDs, PLEDs, and OLECs for the enhancement of penetration of pharmaceutically and/or cosmetically active ingredient(s). The treatment with both unit can be performed in parallel. In addition, it may also be advantageous to first pre-treat the object to be treated with the light source and then to administer the second unit, i.e., the formulated active ingredient(s). It may also be advantageous to first administer the active ingredient(s) and then to attach the said thin light source after a certain time. The present invention also related to a method to enhance the penetration of pharmaceutical and/or cosmetically active ingredient(s) by employing said at least one tin light source which preferably emits light in the red region of the spectrum and/or irradiation in the infrared. The active ingredients and light sources are described elsewhere within the present invention.

A preferred embodiment of the present invention is related to a dermal system, characterized in that the at least one light source is located on a device and the at least one pharmaceutically and/or cosmetically active ingredient represents a spatially different entity.

The dermal system according to the present invention may be any device which is suitable for the intended used as outlined herein. Preferably the said dermal system is characterized in that the device is selected from a flat panel, curved panel, plaster, bandage, blanket, sleeping bag, sleeve, implantable probe, nasogastric tube, chest drain, pad, stent, patch, any kind of clothes, and devices covering at least one tooth in the mouth Further, the present invention relates to said dermal system used as enhancer of penetration of pharmaceutically and/or cosmetically active ingredient(s) preferably through human and animal skin.

Indeed the dermal system can be applied outside or inside the subject to be treated, wherein the subject to be treated is preferably a human or animal subject.

Treatment outside the subject may be, for instance, treatment of the skin, wounds, eye, gingival, mucosa, tongue, hair, nail bed, and nails. Treatment inside the subject may be, for instance, treatment of blood vessels, heart, breast, lung, or any other organ of the subject. Particular devices are required for most applications inside the subject. One such example may be a stent fibers according to the present invention.

Beside the enhancement of penetration the dermal system can also result, as outlined elsewhere within the present invention, in a enhanced action of pharmaceutically and/or cosmetically active ingredients, which is therefore, also subject of the present invention. Enhancement of action by the dermal system, in particular by the thin light source(s) may be due to the enhanced penetration rate of already penetrating active ingredient, by facilitate the penetration of formerly non-penetrating active ingredients and by synergistic effects of the light and/or irradiation emitted by the dermal system and its active ingredient(s).

The dermal system can be used to treat any pharmaceutical and/or cosmetic condition. Preferably the dermal system can be used to treat pharmaceutical (including dermatological) and/or cosmetic conditions which can be treated topically (dermally), transdermally, and/or systemically. Systemic treatment as used herein includes any treatment which makes an active ingredient systemically available such as injection and oral administration. Systemic circulation of an active ingredient may be necessary to get the active ingredient transported to its side of action.

Any disorder and/or cosmetic (aesthetic) condition can be treated with the dermal system enhancing penetration and/or action. This is due to the disclosure of the present invention that the dermal system can facilitate the penetration of active ingredients that have never been before used for dermal application.

Thus, the present invention also relates to said dermal system used for the treatment and/or prophylaxis of diseases and cosmetic conditions. Herein the term diseases includes any pharmaceutical and dermatological diseases.

The following listing is by far not complete and represents only an exemplary selection of possible pharmaceutical and/or cosmetic fields of applications and active ingredients suitable for the use according to the present invention. In fact, one skilled person in the art can, based on the present invention, add without difficulty any pharmaceutical and/or cosmetic application and/or active ingredient not mentioned herein without being inventive.

Preferably the dermal system can be used to in the treatment and/or prophylaxis of inflammatory disorders and/or conditions, fibromyalgia, pain, peripheral pain of shingles (herpes zoster), muscle pain, muscle stiffness, acute and chronic pain (also severe chronic pain), treatment of some types of neuropathic pain, opioid detoxification, sleep disorders, joint care, acute injuries, wound healing, mood disorders, psychological disorders, Morbus Parkinson, Alzheimer's disease, motion sickness (car sickness, airsickness, sea-sickness, centrifguges, dizziness due to spinnin), hypertensive, hypotensive, nicotine addiction, angina, Skin ageing, anti-wrinkle, acne, comedo, psoriasis, atopic dermatitis, cellulite, and arthritis.

The said dermal system can also be used for the application of contraceptives, in the field of hormone therapy to supply hormones through the skin, for the application of anaesthetic, to treat problems associated with osteoporosis, for the application of insect repellents, in the field of disinfection and/or sterilization.

Further preference is given to the treatment and/or prophylaxis of acute and chronic pain, muscle pain, joint stiffness, muscular tension and stiffness, mood disorders, menopause, osteoporosis, angina, acute injuries, arthritis, nicotine addiction, viral infections, inflammation, tumors, cancer.

Further preference is given to the treatment and/or prophylaxis of pain, muscle pain, joint pain, joint stiffness, muscular tension, and muscular stiffness.

Yet another preference is given to the treatment of acne, psoriasis, wrinkles, and skin ageing, particularly if the treatment and/or prophylaxis have predominantly cosmetic/aesthetic aspects.

Very different classes of active ingredients can be employed as part of the dermal system according to the present invention in order to enhance penetration of them for the treatment and/or prophylaxis of the pharmaceutical diseases and/or cosmetic conditions, particularly of them as mentioned above.

These compounds may belong to the following classes selected from compounds for disinfection (e.g. antifungals, antiparasitic active ingredients), anti-inflammatory active ingredients (e.g. steroids, non-steroidal anti-inflammatory active ingredients, immune selective anti-inflammatory derivatives, herbs), active ingredients against itching, anti-psoriasis active agents (e.g. dithranol, psoralene, active ingredients comprising tar extract, calcipotriol), retinoide, active ingredients used for the treatment and/or prophylaxis of acne, skin ageing, wrinkle formation, and or cellulite.

For a more comprehensive list of further medical indications and/or cosmetic fields of interest are disclosed, e.g., in E. Mutschler et al., Arzneimittelwirkungen, Lehrbuch der Pharmakologie and Toxikologie, Wissenschaftliche Verlagsgesellschaft mbH, Stuttgart, 9. Auflage, 2008, in L. Brunton et al., Goodman & Gilman's The Pharmacological Basis of Therapeutics, McGraw-Hill Professional, 11 edition, 2005, and in W. O. Foye et al., Principles of Medicinal Chemistry, Lippincott Williams & Wilkins, fourth edition, 1995.

Preferably the dermal system according to the present invention is a transdermal system. Transdermal absorption is a well-recognized means of drug administration, which benefits from being a non-invasive and convenient way of medicating a patient. Transdermal absorption is a particularly useful means of administration of active ingredients for patients who find other methods difficult or unpleasant. For example, the young and the old can have difficulty with orally administered active ingredients and may find injections particularly unpleasant. Children and patients with dementia can also be difficult to medicate due to lack of compliance. As such, transdermal administration of active ingredients can be a valuable method of administration, especially in the young, the old or mentally impaired patients.

There are currently three major types of transdermal patch systems, namely membrane-controlled systems (see FIG. 1B), adhesive diffusion-controlled systems or matrix systems (see FIG. 1A).

The membrane-controlled system typically consists of four layers: an impermeable backing layer 1, a polymer layer 8 that serves as a drug reservoir, a rate-controlling microporous membrane 9, an adhesive layer 10, and an protective foil 7. The drug reservoir 8 comprises the active ingredient and liquid excipients that encourage absorption of the drug across the skin. Upon application to the skin, the active ingredient diffuses through the membrane and then passes through the adhesive before reaching the skin. The release rate of active ingredient(s) is constant, so, in order to provide the most efficient method of administration, the release rate must be maintained at a level just below the saturation limit of the skin. U.S. Pat. No. 5,683,712 discloses an example of a membrane-controlled system for transdermal administration of homeopathic drugs, wherein a micro-porous membrane is provided for controlling the release of the drug, with a gel containing the drug scattered within the membrane.

The adhesive diffusion-controlled system is very similar to the membrane-controlled system except that the rate-controlling microporous membrane is absent. The system consists instead of an impermeable plastic barrier, a active ingredient reservoir and one or more rate controlling adhesive layers next to the skin. DE 19849823 discloses an example of an adhesive diffusion-controlled system, the plaster comprising a backing layer, a reservoir containing the active ingredient and an adhesive layer overlying the reservoir layer which has non-adhesive regions allowing passage of the active ingredient(s) on contact with the skin.

In the matrix system, the active ingredient reservoir 6 is in direct contact with the skin. As such, the rate of diffusion of the active ingredient(s) is dependent upon the absorption rate of the skin. The system may comprise an impermeable backing layer 1 attached to a active ingredient reservoir consisting of a hydrophilic or hydrophobic polymer containing the dispersed active ingredient. WO 87/00042 describes such a system, for transdermal administration of verapamil at a sustained, substantially uniform rate over an extended period of time. Alternatively, the system may comprise a backing, and an adhesive layer which serves a dual purpose as both the adhesive and the active ingredient reservoir. An example of such a system is described in WO 00/02539, which relates to a plaster containing a non-steroidal anti-rheumatic agent.

If the dermal system represents two spatial different units, as described above, the dermal system represents the light source as a first unit and the formulated active ingredients as a second unit. The first unit may be similar to the transdermal patches or systems as described herein despite the fact, that no reservoir of active ingredients is directly incorporated into it (see FIG. 1C).

The transdermal system according to the present invention comprises in addition to the components of the aforementioned transdermal patches/systems a layer 2 comprising the thin light emitting light source 5, potentially a power supply 3 and potentially a steering unit 4 (see FIG. 1A and FIG. 1B). The light emitting layer can, thus, comprise a power supply which is preferentially an printed battery. Power supply can also occur via an access to an external power supply, such as a battery. In a simple case the dermal system, including the transdermal system and the dermal patch, may not comprise a steering unit and activation of the light source may occur via a switch or by another way to connect the device to the power supply. The steering unit may also be suitable to define an irradiation program, to adjust the wavelength, time of irradiation or the intensity of irradiation. Irradiation can, for example, be on a continuous basis or pulsed.

The transdermal system according to the present invention can be taken any suitable form. In one preferred embodiment, the transdermal system can be taken the form of an adhesive bandage (hereafter "transdermal plaster"). The notable brands, which can be taken as reference, are Band-Aid, Curad, Nexcare, Elastoplast and so on. For example, the transdermal plaster has a backing layer 1, which can be selected from, e.g., woven fabric, plastic, or latex rubber which has an adhesive; the adhesive can be selected from epoxy, which is made from the same compounds as glue. the light source, preferably a thin film light source, is then bonded to the backing layer by the adhesive; the backing layer has small opening(s) allowing electrical contact to the light source; an absorbent pad, for example cotton, which absorbs the active ingredient(s), is then applied to the surface of the light source. The absorbent pad is finally covered with a thin protection plastic sheet.

In another preferred embodiment, the light source can be integrated into the absorbent pad, by using light source in fiber form instead of cotton, for example fiber OLED or fiber OLEC.

The transdermal plaster is applied such that the pad covers the wound, and the fabric or plastic sticks to the surrounding skin to hold the dressing in place and prevent dirt from entering the wound.

The active ingredients as described herein can act in different ways. They can, e.g., be transported across the skin and act systemically. It can also be beneficial to enhance the penetration of topically applied and topically acting active ingredients. The present invention also relates to said dermal system, characterized in that the dermal system is a dermal patch. The intention of a dermal patch is understood herein as to deliver active ingredients to the skin without making it systemically available. Thus, the dermal patch is thought to be used for topical administration. Well known of dermal patches comprise lidocaine or diclofenac. The dermal patches according to the present invention further comprise, as described above, the thin light source and have again a structure as depicted in FIG. 1A to FIG. 1C and the like.

The present invention also relates to the use of the said dermal system for the care, preservation or improvement of the general state of the skin or hair.

The use of the said dermal system for the treatment and/or prophylaxis of time- and/or light- and/or environmental-induced ageing processes of the skin or hair, particularly of dry skin, wrinkle formation and/or pigment defects, and/or for the treatment and/or prophylaxis of the harmful effects of UV rays on the skin is also subject of the present invention.

The more general term skin ageing refers to both the formation of wrinkles and hyperpigmentation. The signs of ageing of the human skin resulting from the effects on the skin of intrinsic and extrinsic factors are defined by the appearance of wrinkles and fine lines, by the yellowing of the skin which develops a wizened appearance along with the appearance of pigmentation blemishes, by a change in the thickness of the skin, generally resulting in a thickening of the stratum corneum and of the epidermis and a thinning of the dermis, by disorganization of the elastin and collagen fibers which causes a loss of elasticity, of suppleness and of firmness, and by the appearance of telnagiectasia.

Some of these signs are more particularly associated with intrinsic or physiological ageing, that is so to say with "normal" ageing associated with age, whereas others are more specific to extrinsic ageing, that is so to say ageing caused by the environment in general; such ageing is more particularly photo-ageing due to exposure to the sun. Other factors causing ageing of the skin are atmospheric pollution, wounds, infections, traumatisms, anoxia, cigarette smoke, hormonal status, neuropeptides, electromagnetic fields, gravity, lifestyle (e.g. excessive consumption of alcohol), repetitive facial expressions, sleeping positions, and psychological stressors.

The changes in the skin which occur due to intrinsic ageing are the consequence of a genetically programmed sequence involving endogenous factors. This intrinsic ageing in particular causes slowing down of the regeneration of skin cells, which is reflected essentially in the appearance of clinical damage such as a reduction of the subcutaneous adipose tissue and the appearance of fine lines or small wrinkles, and in histopathological changes such as an increase in the number and thickness of the elastic fibers, a loss of vertical fibers from the elastic tissue membrane and the presence of large irregular fibroblasts in the cells of this elastic tissue.

In contrast, extrinsic ageing results in clinical damage such as thick wrinkles and the formation of flabby and weather-beaten skin, and in histopathological changes such as an excessive accumulation of elastic substance in the upper dermis and degeneration of the collagen fibers. There are different biological and molecular mechanisms which are responsible for the ageing of the skin and the process is currently not fully understood. However, it was recognized that both intrinsic and extrinsic factors of ageing of the skin share common mechanisms [P. U. Giacomoni et al., Biogerontology 2004, 2, 219-229]. These factors trigger a process leading to the accumulation of damages in the skin resulting in skin ageing since the expression of cell adhesion molecules provokes recruitment and diapedesis of circulating immune cells, which digest the extracellular matrix (ECM) by secreting collagenases, myeloperoxidases and reactive oxygen species.

The activation of these lytic processes provokes random damage of these resident cells, which in turn secrete prostaglandins and leukotrienes. These signaling molecules induce the degranulation of resident mast cells which release the autacoid histamine and the cytokine TNFalpha thus activating endothelial cells lining adjacent capillaries which release P-selectin and the synthesis of cell adhesion molecules such as E-selectin and ICAM-1. This closes a self-maintained micro-inflammatory cycle, which results in the accumulation of ECM damage, i.e. skin ageing.

The dermal system according to the present invention comprising anti-ageing active ingredients can be used in order to enhance the penetration of them. This will either result in an enhanced action and/or in reduced side effects due to lower doses required in order to achieve the same result.

The use of said dermal systems for the treatment and/or prophylaxis of skin unevenness, preferably wrinkles, fine lines, rough skin, large-pored skin, and cellulite is also subject of the present invention. Yet another use for the dermal system according to the present invention is the treatment and/or prophylaxis of vitiligo.

The present invention also relates to that use of the dermal system according to the present invention for the treatment and/or prophylaxis of premature skin ageing, in particular for the treatment and/or prophylaxis of light- or ageing-induced wrinkling of the skin, for the treatment and/or prophylaxis of pigmentation and keratosis actinica, and for the treatment and/or prophylaxis of all diseases which are associated with normal skin ageing or light-induced ageing of the skin.

The present invention also relates to that use of the dermal system according to the present invention for the treatment and/or prophylaxis of skin diseases which are associated with defective keratinisation relating to differentiation and cell proliferation, in particular for the treatment and/or prophylaxis of acne vulgaris, acne comedonica, polymorphic acne, acne rosaceae, nodular acne, acne con□obate, age-related acne, acne occurring as a side effect, acne solaris, medicament-related acne or acne professionalis, for the treatment and/or prophylaxis of other defects of keratinisation, in particular ichthyosis, ichthyosiform states, Darier's disease, keratosis palmoplantaris, leukoplasia, leukoplasiform states, skin and mucosal (buccal) eczema (lichen), for the treatment and/or prophylaxis of other skin diseases which are associated with defective keratinisation and have an inflammatory and/or immunoallergic component, and in particular all forms of psoriasis relating to the skin, mucous membranes and finger- and toenails, and psoriatic rheumatism and skin atopy, eczema, or respiratory atopy, or also hypertrophy of the gums.

The present invention also relates to that use of the dermal system according to the present invention the treatment and/or prophylaxis of all benign or malignant excrescence of the dermis or epidermis, which may be of viral origin, verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare.

The present invention also relates to a method of treating a human or animal with a dermal system according to the present invention. Details of the methods can be directly transferred from what is disclosed within the present invention about the dermal system and the use of the dermal system.

The present invention also relates to the use of a thin light source for the enhancement of penetration of pharmaceutically and/or cosmetically active ingredients through human and/or animal skin, characterized in that the thin light source is selected from OLEDs, PLEDs, and OLECs.

Skin as used herein also includes mucosa, gingival, nail and nail bed as outlined above.

The present invention also relates to a set (kit) comprising of separate packages of
a) A thin light source according to the present invention
b) An active ingredient or a composition of active ingredients or a formulation thereof.

Beside the advantages as outlined within the present invention further advantages of the dermal system according to the present invention can be summarized as follows:

Thin light source allows the preparation of thin and portable devices used for ambulatory treatment.

Treatment with said dermal system can be performed at any time at almost any place without the need to consult a medical professional.

Dermal system is easy to use and can be attached directly to the skin under the clothes and is, thus, very user friendly.

Due to direct contact with the object to be treated lower radiation intensities are required as compared to traditional approaches.

The devices according to the present invention is flexible and can therefore adapt to almost any shape of the object to be treated.

The enhanced penetration rate of active ingredients results in a higher pharmaceutical and/or cosmetic action of the active ingredients.

Due to enhanced penetration side effects of active ingredients can be reduced by lower doses required to achieve the desired systemic or topical concentration.

More, even hydrophilic active ingredients can be administered by the dermal and/or transdermal route.

The dermal system is considered not to disturb the integrity of the skin, which is of importance to fulfil protection functions.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The teaching as disclosed here can be abstracted and combined with other examples disclosed.

Other features of the invention will become apparent in the course of the drawings and of the following description of exemplary embodiments, which are given for illustration of the invention and are not intended to be limiting thereof.

BRIEF DESCRIPTION OF THE DRAWINGS

FIG. 1A shows a Matrix system comprising a backing layer 1, a layer 2 comprising the light source 5 and a power supply 3, a steering unit 4, a self adhesive layer 6 comprising the reservoir with active ingredient(s) dispersed preferably in a polymer matrix, and a protecting foil 7. FIG. 1B shows a Membrane controlled system comprising a backing layer 1, a layer 2 comprising the light source 5 and a power supply 3, a steering unit 4, a polymer layer 8 which is a reservoir comprising the active ingredient(s), a rate controlling micro-porous membrane 9, an adhesive layer 10 and a protecting foil 7. FIG. 1C shows a System in analogy to FIG. 1 a) without layer 6.

WORKING EXAMPLES

Example 1

Materials

The light source of the plaster of the present invention has the following device structure: substrate/anode/buffer layer or hole injection layer/interlayer/emissive layer/cathode and an encapsulation layer. Optionally an additional down-conversion layer on the encapsulation layer can be used in order to further adjust the emission wavelength.

Flexible poly(ethylene naphthalate) (PEN) is used as substrate. ITO is used as transparent anode; PDEOT (Baytron P Al 4083) is used as buffer layer or hole injection layer. HIL-012 by Merck KGaA is used as interlayer.

Different emissive materials are used in the present invention. In one example, an emissive layer comprising red phosphorescent emitter is used, which consisted of a matrix material (PTM-011 by Merck KGaA) and an emissive metal complex (TER-035 by Merck KGaA). In another example, the light source comprises a blue emissive layer and a down-conversion layer. SPB-090, a blue polymer by Merck KGaA, is used as blue emitter, Further for a light source comprising an organic light emitting electrochemical cell (OLEC), poly(ethylene oxide) (PEO) is used as ion conducting material and $LiCF_3SO_3$ as ion source. PEO having a molecular weight of $MW=5\times10^6$ is purchased from Aldrich, and used as received. $LiCF_3SO_3$ (LiTrf) is purchased from Aldrich, and used as received.

Figure 4:
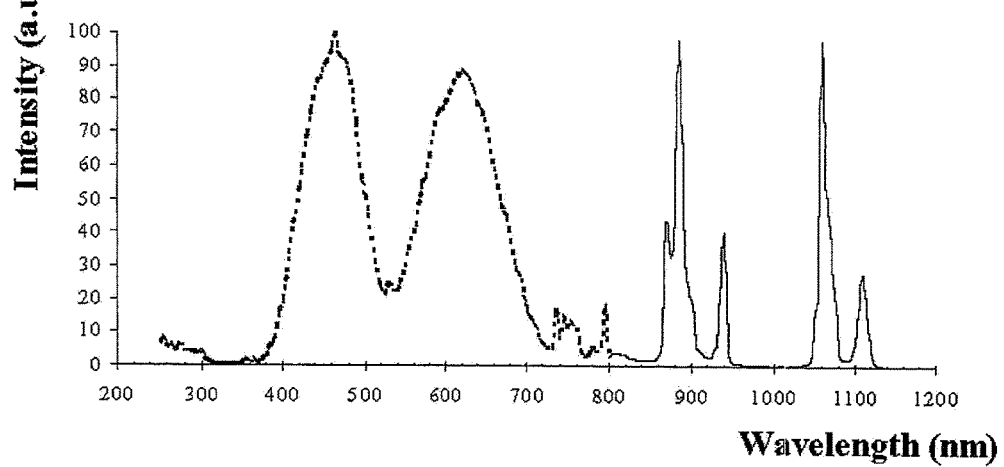
FIG. 4 shows Excitation spectrum (dotted line) and emission spectrum (solid line) of an infrared phosphor, Phos1.

The down-conversion material, Phos1, which in an rare earth gallium aluminate, absorbs blue light and re-emit in infrared light, can be purchased from Phosphor Technology, England, and used as received. The excitation (dotted line) and emission spectrum (solid line) of Phos1 are demonstrated in FIG. 4. The Phos1 has absorption peaks at 465 nm and 620 nm, and emission peaks at 885 nm and 1060 nm.

Example 2

Preparation of Light Emitting Devices

Figure 1A:
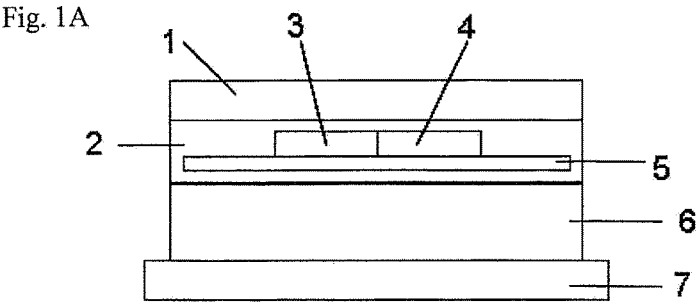
FIG. 1A, FIG. 1B, and FIG. 1C depict different dermal systems (FIG. 1A and FIG. 1B) or parts of a dermal system (FIG. 1C).
Figure 1B:
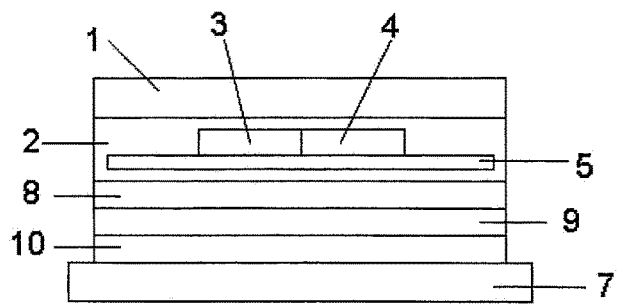
Figure 1C:
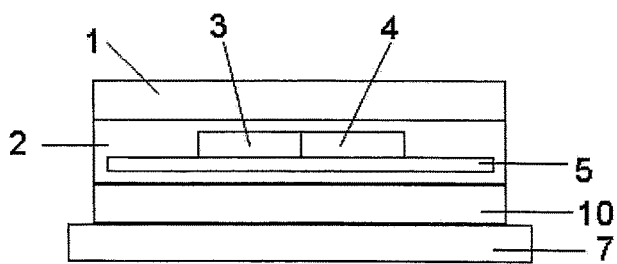
Figure 2:
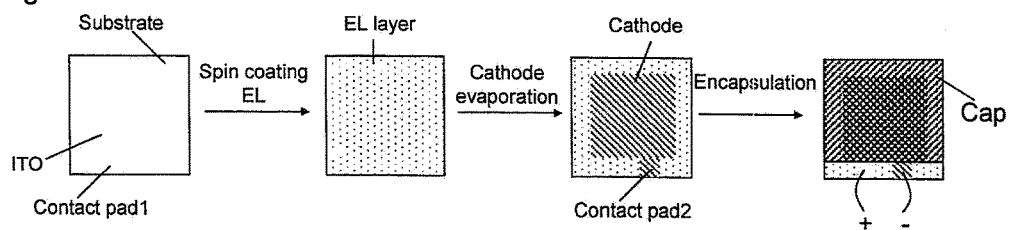
FIG. 2 shows Schema for the preparation of light emitting devices such as OLEDs and OLECs.

The preparation of the light emitting devices, both OLED and OLEC, is schematically shown in FIG. 2.

1) 150 nm ITO is sputtered on PEN using a mask, as shown in FIG. 2. The dimension of the substrate (PEN) and the emissive area is 3×3 cm and 2×2 cm, respectively.

2) PDEOT (Baytron P Al 4083) is deposited as buffer layer with a thickness of 80 nm onto the substrate by spin coating and then heated for 10 min. at 120° C.;

3) 20 nm Interlayer is then deposited on PEDOT by spin coating a HIL012 solution in toluene with a concentration of 5 mg/ml; the interlayer is heated for 60 min. at 180° C. to remove the residual solvent;

4) The emissive layer is deposited by spin-coating in the glove-box. The thickness and the solution used from spin-coating are listed in Table 1. The device is heated to remove residual solvent, the conditions for heat-treatment for different devices are also listed in Table 1.

5) An cathode is deposited by thermal vacuum evaporation onto the emissive layer; The cathode for different devices are also listed in Table 1.

6) The device is encapsulated. Encapsulation of the light emitting devices is achieved using a UV-cured resin, UV Resin T-470/UR7114 (Nagase Chemtex Corporation), and a PEN cap, which is smaller than the substrate to leave the contact pads free, as shown in step 4 of FIG. 2. The UV-resin is applied at first on the edge of the pixel, and the cap is then located on top of them. Then the device is exposed to UV light for 30 seconds. All theses steps are performed are in a glove-box.

| | EL Compostion [wt %] | Solution of EL | | Thickness EL [nm] | Heat-treatment EL min/° C. | Cathode (nm) |
|---|---|---|---|---|---|---|
| | | Solvent | Conc. [mg/ml] | | | |
| Dev1 | 93% PTM-011: 7% TER-035 | 1 | 10 | 80 | 10/180 | Ba(3)/Al(150) |
| Dev2 | 100% SPB-090 | 1 | 10 | 80 | 10/180 | Ba(3)/Al(150) |
| Dev3 | 45% SPB-090: 45% PEO: 10% LiTrf | 2 | 13.75 | 200 | 30/60 | Al(150) |

Solvents: 1 = Toluene; 2 = Chlorbenzene.
Conc.—Concentration. Min./° C.: e.g. 10/180 means 10 minutes treated at 180° C..

Example 3

Characterization of DEV1, DEV2, and DEV3

Devices Dev1 to DEV3 are analyzed according to methods well known to one skilled person. VIL curves and electroluminescent spectrums are recorded.

Figure 3:
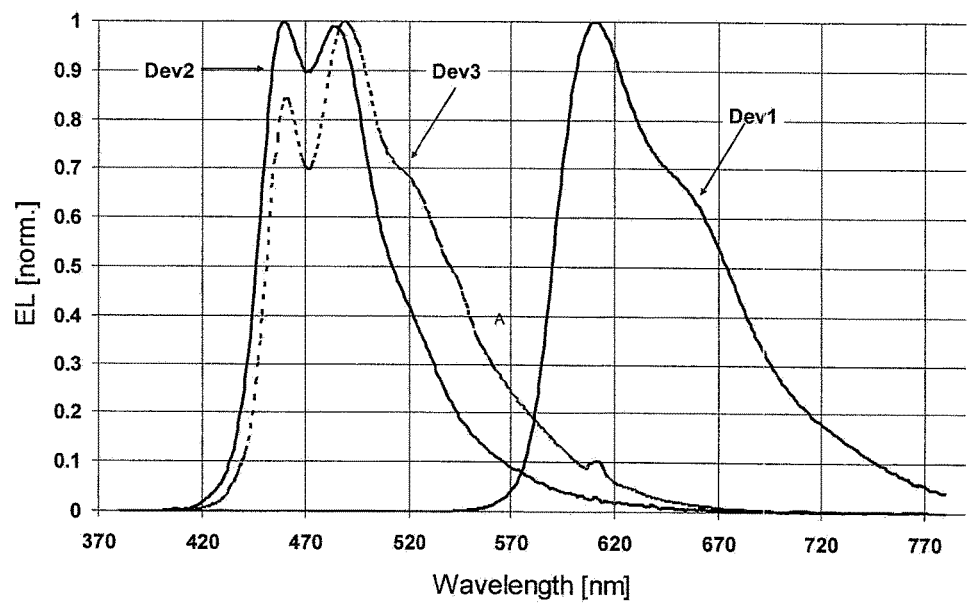
FIG. 3 shows electroluminescent spectra of Dev1-3 according to Example 3.

The electroluminescent spectra of Dev1-3 are shown in FIG. 3. The brightness at 6 V, which can be read from the VIL curves, is 900 Cd/m$^2$ for Dev1, 250 Cd/m$^2$ for Dev2, and 500 Cd/m$^2$ for Dev3.

Example 4

Preparation of Infrared (IR) Emitting Devices DEV4 to DEV6

The IR devices are prepared by using DEV1-3 and the down-conversion phosphor Phos1.

Phos1 is dispersed in a silicone binder. The IR devices Dev4-6 are prepared by dip coating of Phos1 dispersion onto the emitting surface of the devices Dev1-3 of Example 2. The emission spectrum of Dev4-6 are recorded by spectrometer USB2000 (Ocean Optics), which are comparable to the spectrum shown in FIG. 4.

Example 5

Determination of In Vitro Skin Permeation and Skin Hydration

An vitro technique that can be used for the skin permeation analysis is described in detail in L. Simonsen and A. Fullerton, Skin Pharmacology and Physiology 2007, 20, 230-236. In order to validate and compare results of studies according to the present invention with published data, technical settings as disclosed by L. Simonsen and A. Fullerton are employed here as well. The studies as outlined here are, thus, carried out according to methods well known to a person skilled in the art.

Full Thickness skin is removed from the back of pig ears. The subcutaneous tissue is removed and the skin is mounted in open two-chamber Franz-type diffusion cells (diffusion area: 3.14 cm$^{-2}$; recipient volume: 10 ml). Temperature is kept at 32° C. at the skin surface. Recipient phase is a 0.05 M isotonic acetate buffer, pH 4.5, and 2-propanol (80:20%, vol/vol). The experiments are carried out under sink condition.

A test formulation is prepared being a cream containing fusidic acid (20 mg/g) and betamethasone (1 mg/g) as 17-valerate (Fucicort® cream, LEO Pharma). Both active ingredients are commonly used in order to treat atopic dermatitis (AD). The test formulation (4 mg/cm$^2$) is applied to the stratum corneum (SC) side of the skin. The treatment is reapplied at 3, 21, 27, 45, and 51 h, which simulates the actual dosage regimen in patients. At appropriate times (3, 21, 27, 45, 51, and 70 h) a specific amount of recipient phase is withdrawn and replaced by thermostated fluid. Samples are kept at 4° C. for a maximum of 2 days until high-performance liquid chromatography (HPLC) analysis. All permeation experiments are carried out in 6 replicates. The results of the experiments performed by Simonsen et al. can be reproduced within the statistical variance.

The same experiment as described above is carried out. However, the skin is irradiated for 2 h after each application of the cream with the device Dev1 of Example 2. The device is positioned directly above the SC. If the cream is applied or reapplied the light emitting device is repositioned on the SC 5 minutes afterwards. After having the skin irradiated for 1 h, the irradiation source is removed from the skin. Again samples of the recipient are taken and analyzed by HPLC in time intervals given above. Permeation is significantly ($p<0.005$) improved for both fusidic acid and betamethasone. As compared to the control experiment permeation of fusidic acid is enhanced for 16% and that of betamethasone is enhanced by 14%.

The same experiment as described above is carried out. Again, the skin is irradiated for 2 h after each application of the cream, but with the devices Dev4-6 of Example 4 in three separate runs, one run for each device. The devices are positioned directly above the SC. If the cream is applied or reapplied the light emitting device is repositioned on the SC 5 minutes afterwards. After having the skin irradiated for 1 h, the irradiation source is removed from the skin. Again samples of the recipient are taken and analyzed by HPLC in time intervals given above. Permeation is significantly ($p<0.005$) improved for both fusidic acid and betamethasone. As compared to the control experiment permeation of fusidic acid is enhanced for more than 29% and that of betamethasone is enhanced by more than 27% for all three IR devices (Dev4-6).

The same experiment as described above is carried out. However, the skin is irradiated for specific time intervals throughout the experiment with the device Dev5 of Example 4. The device is positioned directly above the SC. The device is positioned 5 minutes after application of the cream and skin is irradiated for 30 min. Afterwards the light emitting device is removed from the SC. Again samples of the recipient are taken and analyzed by HPLC. Despite short irradiation times, skin permeation is significantly ($p<0.005$) improved for both fusidic acid and betamethasone. As compared to the control experiment permeation of fusidic acid is enhanced for 24% and that of betamethasone is enhanced by 20%.

Furthermore hydration of the epidermis can be determined by corneometry. As described above skin of the back of pig ears is mounted in open two-chamber Franz-type diffusion cells. The experiment is carried out in analogy to the ones described above and according to methods well known to one skilled in the art, but without any cream applied. The evaluation of the moisture of the skin is undertaken with a corneometer, whereby the capacity measurements through the SC is used. Corneometric measurements are performed before and immediately after irradiation. Hydration of the epidermis is measured after having irradiated the SC with the device Dev5 of Example 4 for 30 min. All experiment are carried out three times. Hydration of the irradiated skin is improved by 22% ($p<0.005$).

The invention claimed is:

1. A dermal system comprising at least one light source and at least one pharmaceutically and/or cosmetically active ingredient used for the enhancement of penetration and/or action of the at least one pharmaceutically and/or cosmetically active ingredient, characterized in that the least one light source is a thin light source comprising at least one inorganic light emitting diode (LEDs) and/or at least one organic light emitting device;

wherein the at least one light source further comprises a down conversion medium, which absorbs the light from said light emitting device, and re-emits infrared radiation with wavelength in the range between 700 nm and 3 mm, wherein the at least one light source emits infrared irradiation with a maximum emission in the range between 700 nm and 3 mm;

wherein the dermal system further comprises a backing layer, a layer comprising the at least one light source and a power supply, a self adhesive layer comprising the at least one pharmaceutically and/or cosmetically active ingredient, and a protecting foil; and wherein the dermal system is not a photodynamic therapy system.

2. The dermal system according to claim 1, characterized in that the thin light source comprises an organic light emitting device selected from the group consisting of organic light emitting diodes (OLEDs), polymer light emitting diodes (PLEDs) and organic light emitting electrochemical cells (OLECs).

3. The dermal system according to claim 1, characterized in that both the at least one light source and the at least one pharmaceutically and/or cosmetically active ingredient are assembled in the same device.

4. The dermal system according to claim 1, characterized in that the at least one light source is located on a device and the at least one pharmaceutically and/or cosmetically active ingredient represents a spatially different entity.

5. The dermal system according to claim 3, characterized in that the device is selected from the group consisting of a flat panel, curved panel, plaster, bandage, blanket, sleeping bag, sleeve, implantable probe, nasogastric tube, chest drain, pad, stent, patch, any kind of clothes, and devices covering at least one tooth in the mouth.

6. The dermal system according to claim 1 wherein the dermal system is an enhancer of penetration of pharmaceutically and/or cosmetically active ingredients through human and animal skin.

7. The dermal system according to claim 1 wherein the dermal system is an enhancer of action of pharmaceutically and/or cosmetically active ingredients.

8. The dermal system according to claim 1 for the treatment and/or prophylaxis of acute and chronic pain, muscle pain, joint stiffness, muscular tension and stiffness, mood disorders, menopause, osteoporosis, angina, acute injuries, arthritis, nicotin addiction, viral infections, inflammation, tumors, and cancer.

9. The dermal system according to claim 1, characterized in that the dermal system is a transdermal system.

10. The dermal system according to claim 1, characterized in that the dermal system is a dermal patch.

11. A method comprising treating skin or hair with the dermal system according to claim 1 for the care, preservation or improvement of the general state of the skin or hair, wherein the infrared radiation re-emitted by the down conversion medium enhances the penetration of the at least one pharmaceutically and/or cosmetically active compound.

12. The method according to claim 11 for the treatment and/or prophylaxis of time- and/or light- and/or environmental-induced ageing processes of the skin or hair.

13. The method according to claim 11 for the treatment and/or prophylaxis of skin unevenness.

14. The method according to claim 11 for the treatment and/or prophylaxis of premature skin ageing.

15. The method according to claim 11 for the treatment and/or prophylaxis of skin diseases which are associated with defective keratinisation relating to differentiation and cell proliferation.

16. The method according to claim 11 for the treatment and/or prophylaxis of all benign or malignant excrescence of the dermis or epidermis.

17. A method comprising treating a human or animal with the dermal system according to claim 1.

* * * * *